United States Patent [19]

Schwan

[11] 4,382,140

[45] May 3, 1983

[54] 2,4-DIPHENYL-5-PYRIMIDINECARBONITRILE

[75] Inventor: Thomas J. Schwan, Norwich, N.Y.

[73] Assignee: Norwich Eaton Pharmaceuticals, Inc., Norwich, N.Y.

[21] Appl. No.: 342,739

[22] Filed: Jan. 26, 1982

[51] Int. Cl.³ .................. C07D 237/24; A61K 31/505
[52] U.S. Cl. ..................................... 544/242; 424/251
[58] Field of Search ........................................ 546/242

[56] References Cited

U.S. PATENT DOCUMENTS 3,944,581  3/1976  Schwan ............................. 544/242
3,969,355  7/1976  Schwan ............................. 544/242

*Primary Examiner*—Donald G. Daus
*Assistant Examiner*—Diana G. Rivers
*Attorney, Agent, or Firm*—Anthony J. Franze

[57] ABSTRACT

2,4-Diphenyl-5-pyrimidinecarbonitrile is useful as an immunomodulating agent.

1 Claim, No Drawings

2,4-DIPHENYL-5-PYRIMIDINECARBONITRILE

This invention is concerned with chemical compounds and more particularly with the compound 2,4-diphenyl-5-pyrimidinecarbonitrile (I) useful as an immunomodulating agent.

An immunomodulating agent is a substance which regulates or otherwise affects the immune response of a host. Compounds having such capability are useful as drugs for mitigating the immunological incompetence of a host body often times encountered as an undesired side effect of cancer chemotherapy involving antineoplastic agents. Such depressed immune response lessens the protective function of the immune system permitting the invasion of pathogens such as viruses, bacteria and other parasites which otherwise could be resisted.

The compound of this invention exhibits salutary effect upon the immune system of an animal with respect to resistance to bacterial infection when such system has been depressed by administration of an antineoplastic. Thus, 75% or more of mice administered intraperitoneally 100 mg/kg of cyclophosphamide 4 days before being inoculated intravenously with $1 \times 10^5$ cells of *Pseudomonas aeruginosa* died. In mice not receiving cyclophosphamide, the mortality was about 40%. When the compound of this invention was administered at a level of 40 mg/kg subcutaneously to cyclophosphamide (150 mg/kg) treated mice at days 4 and 2 before inoculation with *Pseudomonas aeruginosa*, there was a survival of about 55%.

In order that this invention may be readily available to and understood by those skilled in the art, the following example sets forth the now preferred method of its preparation.

To a solution of 6.96 g (0.04 mole) of benzamidine hydrochloride hydrate in 300 ml methanol was added quickly 8.56 g (0.16 mole) sodium methoxide. The solution was stirred for 5 min at ambient temperature and 8.04 g (0.04 mole) of 2-ethoxymethylenebenzoylacetonitrile was added. The mixture was stirred at ambient temperature for 2 hours, diluted with 1000 ml cold water, stirred for 1 hour and filtered. The solid was washed with $2 \times 100$ ml portions of water, air dried and dried at 60° for 3 hours to give 9.33 g (90%) of the product, m.p. 145°–149°.

Recrystallization from ethanol gave an analytical sample, m.p. 147°–150°.

Anal. Calc'd. for $C_{17}H_{11}N_3$: C, 79.36; H, 4.31; N, 16.33; Found: C, 79.34; H, 4.30; N, 16.22.

What is claimed is:

1. The compound 2,4-diphenyl-5-pyrimidinecarbonitrile.

* * * * *